United States Patent [19]

Jeter et al.

[11] Patent Number: 5,800,534
[45] Date of Patent: Sep. 1, 1998

[54] BREAST ENHANCEMENT APPARATUS AND METHOD

[75] Inventors: John D. Jeter, 1403 Teche Dr., St. Martinville, La. 70582; James J. Fournet, Lafayette, La.

[73] Assignee: John D. Jeter, St. Martinville, La.

[21] Appl. No.: 874,523

[22] Filed: Jun. 13, 1997

Related U.S. Application Data

[62] Division of Ser. No. 570,700, Dec. 11, 1995, Pat. No. 5,683,420.

[51] Int. Cl.$^6$ ........................... A61F 2/12
[52] U.S. Cl. ........................... 623/8; 128/898
[58] Field of Search ........................... 606/234; 128/898; 623/6, 7, 8

[56] References Cited

U.S. PATENT DOCUMENTS

| | | | |
|---|---|---|---|
| 3,382,867 | 5/1968 | Reaves | 128/38 |
| 5,066,303 | 11/1991 | Bark et al. | 623/8 |
| 5,099,830 | 3/1992 | Kishimoto | 128/38 |
| 5,125,910 | 6/1992 | Freitas | 604/249 |
| 5,219,360 | 6/1993 | Georgiade | 623/8 |
| 5,258,026 | 11/1993 | Johnson et al. | 623/8 |

*Primary Examiner*—Michael Buiz
*Assistant Examiner*—Kevin Truong
*Attorney, Agent, or Firm*—John D. Jeter

[57] ABSTRACT

The human breast is enhanced by enlargement by inserting body compatible fluids into the natural lactatous containments within the breast by flowing the liquid into the lactatous duct openings at the nipples. Flow is induced, from a source of pressurized fluid, by directing a jet of liquid into the duct opening, by pressing the fluid conductor against the opening or by penetrating the opening with a blunt needle or equivalent catheter. To ease penetration of the opening, suction apparatus is offered that distends the nipple to straighten the duct. Plugs are offered to enhance the fluid retention ability. The plug may be solid or valved to allow fluid flow only when a handling tool is inserted to manipulate the plug. Fluid emulsification apparatus is provided to condition fluids which may include saline aqueous liquid, compressible fluid, and autogenous materials individually or in combinations.

6 Claims, 3 Drawing Sheets

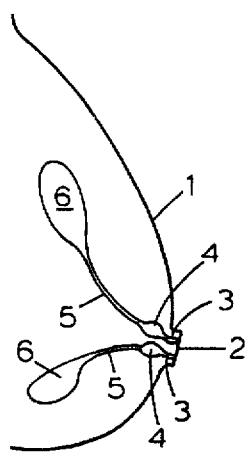
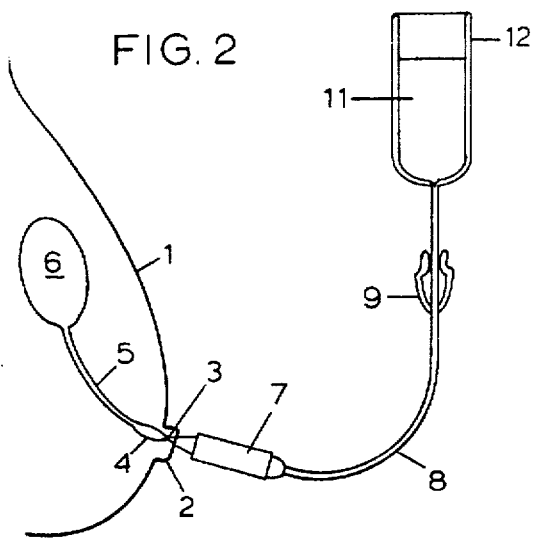
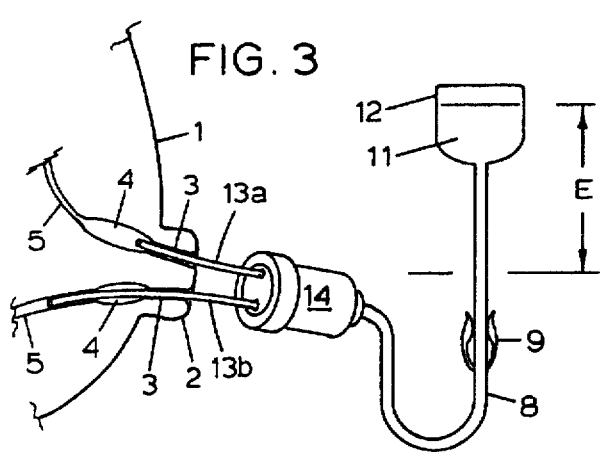
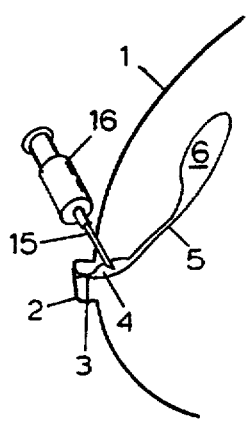
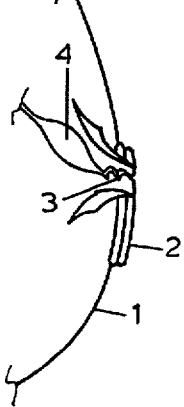
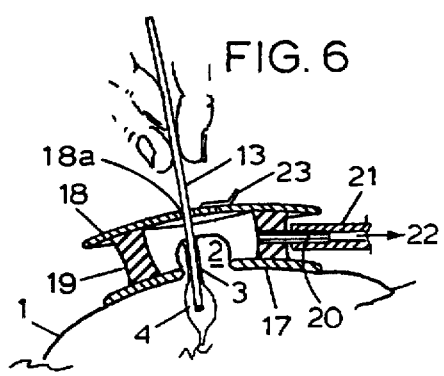

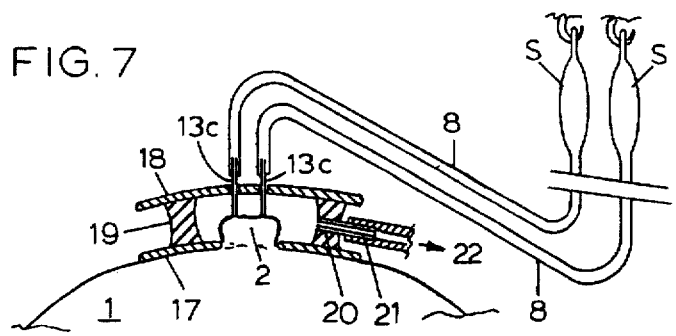
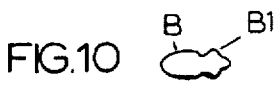
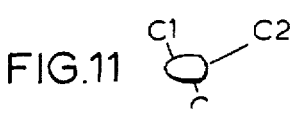
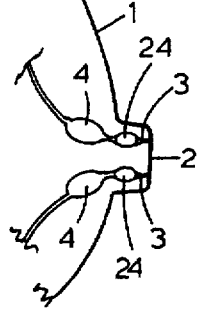
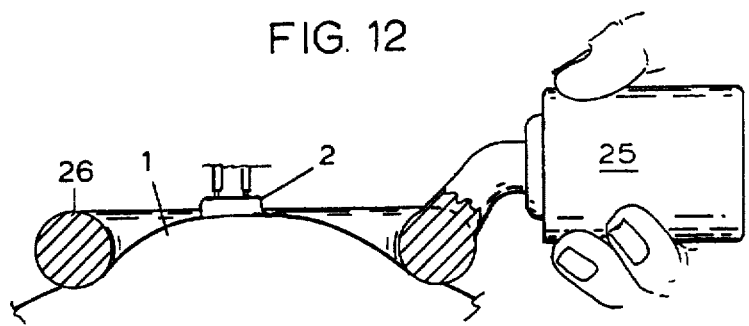
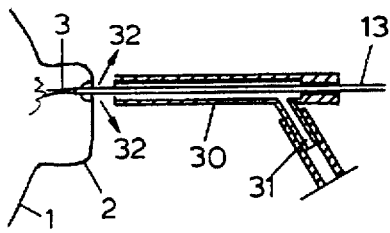
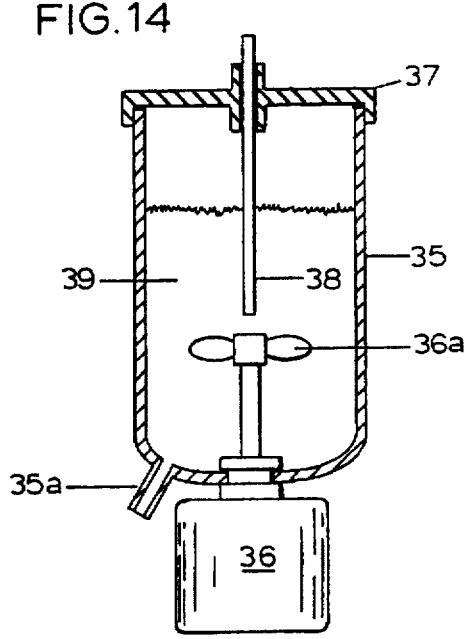

BREAST ENHANCEMENT APPARATUS AND METHOD

This application is a division of application Ser. No. 08/570,700, filed Dec. 11, 1995 U.S. Pat. No. 5,663,420.

This invention pertains to human breast enhancement and more particularly to enlargement of the breast by the placement of enhancement fluids within the natural fluid reservoir, or containment definable as the gland lobule and related lactatous ducts, by injection of fluid into the apertures of the nipple.

BACKGROUND

At the present time breast configuration enhancement is being provided by surgically implanting a sac of fluid between the existing breast and the rib cage to push the visible portion of the breast outward. The implant can only be removed surgically. The presence of an implanted body of foreign material is now a cause for concern and a better method is needed to satisfy the utility defined by an expensive and controversial practice now existing.

It is desirable to depart as little as possible from natural process to achieve desired results and a fluid sac arrangement is natural to the system in the breast. The breast is capable of producing milk, storing the milk and delivering it to the nipples upon demand. This capability has provided a reservoir, related ducts, and a non intrusive entry port needed for artificial enhancement by inserting tissue compatible fluid in the opposite direction. Fluid compatible with the host tissue is essential but the insertion is practical.

It is therefore an object of this invention to provide a breast enhancement procedure for inserting fluids into the lactiferous duct, ampulla, connective duct, and into the gland lobule.

It is another object of this invention to provide breast enhancement apparatus and procedures to inject fluid into existing holes on the nipples with a pressure limit that precludes the possibility of moving fluids into the blood stream.

If is yet another object to provide procedures for breast enhancement by injecting enhancement fluid into the ampulla by way of penetration of the skin with a needle to inject the fluid into the ampulla for distribution into the gland lobule.

It is still another object to provide apparatus and procedure for breast enhancement by introduction of enhancement fluids into the breast by catheter insertion into the natural holes in the nipples and at least into the lactiferous duct.

It is a further object of this invention to provide means to close the ducts in the nipples with tissue compatible material arranged for easy removal.

It is yet another object to provide vacuum apparatus to distend the nipple to straighten the lactiferous duct for ease the insertion of a catheter or blunt needle into the lactiferous duct.

It is still another object of this invention to provide means to permeate the breast tissue with vibration to induce fluid distribution within the breast during the installation of enhancement fluid.

It is another object to provide compatible enhancement fluids that are natural to the receiving body and compatible with all body tissue.

It is still another object to provide compatible breast enhancement fluids that reduce the absorption rate of those fluids from the enhanced breast, at least some of which may be autogenous materials.

It is yet another object of this invention to provide apparatus and procedures for the emulsification of air, or other suitable gas, into breast enhancement fluids to reduce specific gravity of the fluids and to provide a mild sustaining pressure to reduce the tendency for the enhanced breast to sag.

These and other objects, advantages, and features of this invention will be apparent to those skilled in the art from a consideration of this specification, including the attached claims and appended drawings.

SUMMARY

The novel procedure for breast enhancement involves normal clinical practice in cleaning the nipples before fluid insertion. In the preferred manner of fluid installation no tissue is broken and insertion, rather than injection, is the appropriate term. There are four options for flowing compatible fluid from a supply reservoir to the reservoirs in the breast. The easier choice is to apply light force upon a small nozzle to seal it against the nipple to direct flow into a selected nipple opening from a supply of breast enhancement fluid connected to the nozzle. The second choice involves the use of a blunt needle that cuts no tissue but does enter the nipple opening to extend some distance along the associated duct. The third option involves the use of a catheter that extends from a manual control into the nipple opening and along the lactiferous duct to at least the ampulla and flowing the inserted liquid along the catheter. The fourth option involves needle penetration of the dermal cover and into the ampulla and injecting enhancement fluid.

The nipple sometimes tends to shrink and fold the lactiferous duct such that it is reluctant to receive a blunt needle or catheter. To distend the nipple and straighten the duct apparatus is provided to apply a moderate vacuum to the nipple. The preferred apparatus comprises, in effect two watch glasses with an elastomer ring between the two providing some separating space. One watch glass has a hole to receive the nipple and bear against the breast. The second watch glass has a plurality of holes to receive catheters or blunt needles. The elastomer ring has a duct for the introduction of a moderate vacuum between the watch glasses. The holes in the outer watch glass can be plugged or covered by a thin tab of rubber sheet until ready for the insertion of a catheter. When the nipple is distended, each hole can be opened by removal of a plug or tab and a catheter is inserted through that hole and into the aligned duct while the moderate vacuum is sustained. By repeating the process, all catheters can be inserted independently into aligned ducts. Enhancement fluids can be fed independently to each catheter or all catheters can be fed from a common reservoir. Reservoir pressure can be safely sustained by elevating the reservoir or by applying moderate and limited air pressure to a suitable reservoir to propel the fluid into the catheters.

Fluid can be delivered into the breast without contacting the surface of the breast by impinging a jet of enhancement fluid against the opening of the lactiferous duct at the nipple. The jet represents fluid pressure converted to velocity and the velocity is converted back to pressure when the jet is stopped by impingement. If the point of impingement is the duct opening the pressure exists in the duct and does not bear upon the surrounding area. The duct is dilated and fluid is accepted if the duct is receptive. This procedure is devoid of preferred volume and installation pressure controls but does provide access to some problem lactiferous ducts.

In some cases there may be inadequate resistance, natural to the breast, to prevent unaccustomed pressure from causing the inserted fluid to be expelled from the nipple openings. For these occasions a small plug having a generally oblong shape of acceptable size and compatible material is urged into the nipple orifice and some distance along the lactiferous duct. The tissue closes around the smooth plug and resists its movement along the duct. It stays in place in the usual situation but the application of an astringent such as alum to the nipple end further tends to hold the plug in place. The plug can be squeezed out of the duct by acceptable finger pressure.

In the breast not modified by lactation, fat deposits may provide tortuous paths for the ducts related to each gland lobule and insertion of fluid new to the overall breast structure may produce unusual breast conformation. This can be somewhat corrected, especially during fluid insertion, by the application of vibration that apparently causes relative movement between tissue masses and allows fluid to pass in areas that would normally be restricted or blocked.

Most liquids natural to the body are absorbed by the body from concentrated deposits much as lactated fluids are eventually absorbed from the inactive breast. There are fluids that are tissue compatible and are only very slowly absorbed by the body. It is these fluids, known as isotonic fluids, that may now be used safely for enhancement. Such fluids are currently available in quantity, and are United States government approved for injection into the body. With the disclosed procedure being applied new and more specifically applicable fluids will most likely be made available. That is contemplated by and is within the scope of the claims.

To reduce the specific gravity of the inserted fluid some air or other gas may be used. The gas is best applied by first emulsifying it with the liquid to be inserted. Finely emulsified, the gas is slow to aggregate into larger bubbles and to separate from the liquid. Once the two phase fluid is installed in the small interstices of the breast it tends to stay in place and cannot be readily distinguished by sensory processes. This is especially true when autogenous fat and compressible fluids are emulsified. The volumetric percentage of gas needed to satisfactorily reduce the specific gravity of the installation is small and even doubling the gas volume due to ambient pressure change, even large altitude changes, indicate no resulting problems.

Autogenous materials assure host compatibility with materials added to most parts of the body and the breast is no exception. Fat, for instance, from other parts of the body may be used to make up at least part of the enhancement fluid. To facilitate insertion into the breast, emulsification with saline solution is a convenient process. An emulsion of fat and compressible fluid offers a stabilizing option and it is inserted by the same procedure and by the same apparatus already described herein. In many cases it is desirable to assure that enhancement fluids be readily removable to restore the original condition to the lactatous system and emulsification of autogenous materials with other fluids appear to enhance that option, at least on a reasonably short term basis.

BRIEF DESCRIPTION OF DRAWINGS

In the drawings wherein like features have similar captions FIG. 1 illustrates the usual breast structure.

FIG. 2 is a side view, with a sagittal view of the breast, and illustrates the simplest form of the enhancement fluid insertion apparatus.

FIG. 3 is a side view, with a sagittal view of the breast, and illustrates an alternate apparatus using catheters to insert enhancement fluid into the breast.

FIG. 4 is a side view, with a sagittal view of the breast, and illustrates the use of a penetrating needle to inject enhancement fluid onto the breast.

FIG. 5 is a sagittal view of a breast with the anatomical features abbreviated showing a common problem found when using the lactatous duct for fluid insertion.

FIG. 6 is a side view of a nipple erecting appliance prepared for use in aiding the installation of enhancement fluid insertion apparatus.

FIG. 7 is a view similar to that of FIG. 6 with fluid insertion apparatus in place.

FIG. 8 is a sagittal view, anatomically abbreviated, of the breast with lactatous ducts occluded by apparatus of this invention.

FIGS. 9, 10, and 11 are side views of three preferred forms of occluding apparatus shown in FIG. 8.

FIG. 12 is a side view of a ring vibrator preferred for use in facilitating distribution of enhancement fluid within the breast.

FIG. 13 is a side view, somewhat enlarged and mostly in cut away, of a single catheter with a surrounding tube to aid in catheter acceptance into the duct.

FIG. 14 is a side view, mostly in cut away, of an emulsifier accessory for conditioning the enhancement fluid.

DETAILED DESCRIPTION OF DRAWINGS

Figure 15:
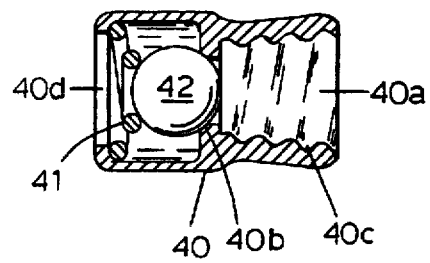
FIG. 15 is a side view, mostly cut away and rather enlarged, of a valve for the lactiferous duct.

In the drawings, some details common to apparatus construction but well within the art and not bearing upon points of novelty are omitted in the interest of descriptive clarity and efficiency. Such omissions may include pins, washers, threaded fasteners and junctions, and the like.

In FIG. 1 a sagittal view of the breast is shown in the usual, but abbreviated, anatomical format. There are usually several independent lactatous systems present but only two are shown to illustrate primary features that affect the design of apparatus of this invention. The breast 1 has the nipple 2 with apertures operable to the lactiferous ducts 3 which have enlargements 4, called ampulla, connected with the connective ducts 5 extending to the gland lobules 6. Each connected set of features 3, 4, 5, and 6 comprise one of the average breasts several independent lactatous systems as defined herein.

In FIG. 2 a simple form of enhancement fluid insertion apparatus includes nozzle 7 supplied fluid by tube 8, controlled by clamp 9, with enhancement fluid from reservoir 11 in container 12. Fluid flows from the nozzle into an aperture of the nipple 2 common to duct 3, through ampulla 4, along connective duct 5 into the gland lobule 6 to enlarge breast 1.

In FIG. 3 the usual breast 1 and nipple 2 are shown with two lactatous systems to illustrate use of two catheters 13a and 13b to insert enhancement fluids. The first catheter 13a extends through the lactiferous duct 3 and opens into the ampulla 4. This exposes the ampulla to the inflowing pressure and, in some cases can cause unsightly enlargement of the breast near the nipple. Catheter 13b is inserted to extend well into the connective duct 5. This prevents exposure of the ampulla to the inflowing pressure. Both catheters, in any one case, will probably be used alike but are as shown for descriptive convenience. The catheters are shown to be fed fluid from a common feed septum 14 served by a common reservoir 11 in container 12 by way of tube 8, controlled by clamp 9. Pressure available to the catheters is limited to the fluid head E to prevent excess pressure consequence.

FIG. 4 shows the usual sagittal section, anatomically abbreviated, with a piercing needle 15 inserted through the dermal cover of the breast to and into the ampulla. Syringe 16 is shown for inclusion of possible reservoirs. The other reservoirs disclosed herein can be used to feed fluid to the needle 15. This use of a piercing needle is an optional procedure that is of secondary interest but it is anticipated by and is within the scope of the claims.

FIG. 5 illustrates a problem that may be encountered in traversing the lactiferous duct with blunt needles or catheters. The nipple 2 tends to shrink in length and contributes to the fluid retention ability of the lactiferous duct by folding or creasing the duct. That impedes entry into the duct when the penetrating device encounters a fold.

FIGS. 6 and 7 illustrate means to straighten the lactiferous ducts that experience the problem shown in FIG. 5. A watch glass 17 or similar member has a hole in it to accept the nipple and bears upon the breast. An elastomer ring 19 serves as a spacer between watch glass 17 and watch glass 18 such that watch glass 18 remains somewhat above the nipple when it is distended. A moderate vacuum is applied to the ring between the watch glasses and causes the nipple to distend, straightening the lactiferous ducts. Watch glass 18 has a plurality of holes illustrated by 18a to accept the catheter or blunt needle and they are individually covered by a thin rubber sheet tab 23. Rubber plugs can be used instead of tabs if preferred. Ring 19 may be adhered to watch glass 17 but watch glass 18, somewhat lubricated, rests atop the ring and it can be moved laterally to align selected holes 18a with apertures in the nipple. Each tab is removed when the related hole is properly positioned and a blunt needle or catheter is inserted and moved into the lactiferous duct. A catheter 13 is shown in FIG. 6. When the catheters are all inserted they can all be collectively inserted into holes in the collector septum 14 shown in FIG. 3. Tube 8 serves the function previously described herein. As shown in FIG. 7 the catheters or blunt needles, blunt needle 13 shown, can be fed by individual supply tubes 8 which can be individually supplied with fluid from flexible bags S shown in the background.

FIG. 8 shows the use of plugs 24, preferably formed from gold dental wire, with a final oval shape inserted into the lactiferous duct. The plugs resist movement along the duct but can be removed by applying finger pressure at the back of the nipple. This plug prevents enhancement fluid from flowing out of the breast until the breast adapts to the change in shape and pressure.

FIGS. 9, 10, and 11 show three preferred types of plugs each insertable with a thin walled tube with an outside diameter about the same as the diameter of the plug. The tube is immediately removed. Shape A moves with little force in either direction within the duct. Shape B with convolutions B1 holds position more firmly. Shape C, more sharply tapered C1 on the left end and a more abrupt taper C2 on the right end moves to the right when subjected to lateral squeezing of the duct it serves.

FIG. 12 shows a hand held vibrator 25 fitted with a ring 26 that oscillates the globules within the breast while enhancement fluid is being installed. The breast internal structure is probably never geometrically distributed in perfect order but time, activity, and the pendulous weight causes such relative position changes that the connective ducts may be pinched against fluid flow. The lactating breast seems to work these problems out in time but the rather short term changes related to enhancement offers no such time. The vibrator enhances the flow distribution by temporarily and frequently changing any flow interference. The ring can surround the watch glasses, if used, and does not impede their function.

FIG. 13 shows apparatus and procedure for easier insertion of a catheter 13 into a nipple aperture. The catheter is first pushed against the aperture surface. A stream of water, not destined for installation in the breast, is then projected from tube 30 against the aperture. The aperture tends to open and accept the catheter. This flow is wasted by streams 32. Finally, the tube 30 is slipped off the catheter after the catheter is in place.

FIG. 14 shows a blender type high speed emulsifier, driven by motor 36, for the mixing of air, or other suitable gas, admitted by tube 38 into the enhancement fluid 39 in the reservoir 35. The air serves two purposes. It reduces the specific gravity of the enhancement fluid and it is compressible to retain a reasonable pressure within the enhanced breast to reduce the tendency for the enhanced breast to promptly sag. Impeller 36a, spinning at high speed induces air to be drawn through tube 38 into the fluid. When finely emulsified, the air is slow to aggregate into larger bubbles and the fluid changes little in the time needed for insertion into the breast by way of tube 35a. Compressible fluid is especially stable in autogenous fat when finely emulsified. Lid 37 prevents splash and supports tube 38.

Figure 16:
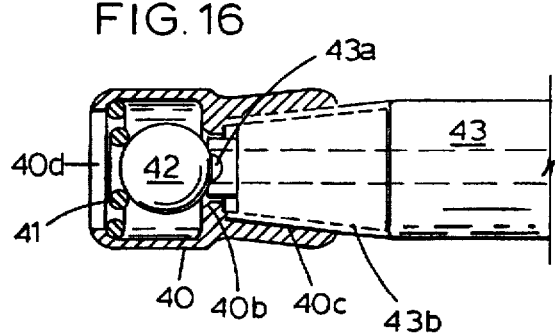
FIG. 16 is identical to FIG. 15 except for an installation and service tool in the usual use situation.

FIGS. 15 and 16 show a check valve, normally about one millimeter in diameter, for use in the lactiferous duct, to provide simplicity in long term care. Body 40 has a channel extending axially and comprising threaded opening 40a, valve seat 40b, and opening 40d. Spring 41 urges ball 42 against seat 40b to prevent flow of fluid to the right which will be toward the nipple outlet of the duct. Hollow tool 43 has a tapered thread 43b to mate with threads 40c. When the tool is threaded into the body 40 a protuberance on the tool 43c lifts ball 42 off the seat and fluid can flow in either direction through the valve and tool which is tubular. Notch 43a prevents the ball from sealing the bore of the tool. Efforts are now being made to devise the valve entirely of compatible plastic with the movable element, equivalent to ball 42, molded as part of the body. This will not change the essence of the functional description and the configuration will be much as shown.

Figure 17:
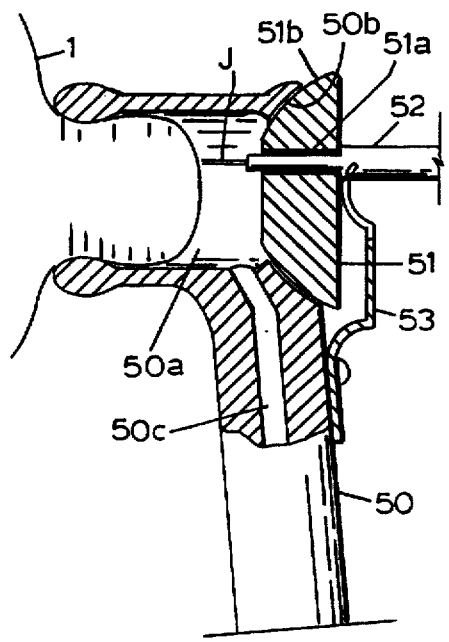
FIG. 17 is a side view, mostly cut away, of an alternate form of the apparatus for fluid installation.
Figure 18:
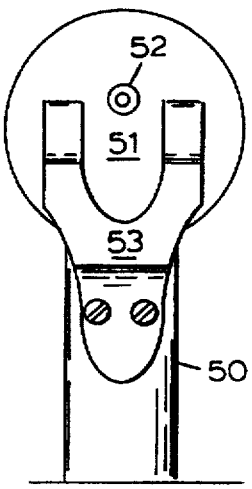
FIG. 18 is a view from the right side of FIG. 17.

FIGS. 17 and 18 show apparatus for injecting fluid into troublesome lactatous ducts by velocity induced internal pressure. A jet J of enhancement fluid is projected from tube 52 to impinge against a duct opening (not shown) at the nipple surface. In an impinging jet the velocity head is converted back to pressure which is internal to the duct and the impinged fluid will flow along the now opened channel. Another form of nipple lifting suction appliance is shown with no surface bearing upon breast 1. Nipple 2 is drawn into the opening 50a by mild suction admitted along bore 50c of the handle 50. Cover 51 has spherical surface 41b resting on mating surface 50b with hole 51a to accept tube 52. Spring clip 53 holds cover 51 in place in the absence of suction in opening 50a.

The use of air, or other gas, as an enhancement fluid is part of this disclosure, especially as a short term aid for the breast to accommodate change before the fluid is changed out to liquid. That is anticipated by and is within the scope of the claims.

Selective distribution of fluid among the plurality of lactiferous systems permits some latitude in attending to the aesthetic amenities important to many patients seeking breast enhancement. The selective use of compressible enhancement fluids further contributes to the aesthetic enhancement possibilities offered by the apparatus and procedure of this invention.

From the foregoing, it will be seen that this invention is one well adapted to attain all of the ends and objects hereinabove set forth, together with other advantages which are obvious and which are inherent to the tool.

It will be understood that certain features and sub-combinations are of utility and may be employed without reference to other features and sub-combinations. This is contemplated by and is within the scope of the claims.

As many possible embodiments and steps may be made of the apparatus and procedures of this invention without departing from the scope thereof, it is to be understood that all matter herein set forth or shown in the accompanying drawings is to be interpreted as illustrative and not in a limiting sense.

The invention having been described, we claim:

1. A procedure for enhancement of the contour of the human breast by installing enhancement fluids in containments provided by the lactatous systems, comprising the steps:
   a) providing a source of fluid under pressure;
   b) delivering said fluid to a nozzle;
   c) directing said fluid from said nozzle into at least one lactatous duct opening in the nipple and allowing an amount of said fluid to flow into a containment.

2. The procedure of claim 1 wherein said fluid is a saline solution of the isotonic class.

3. The procedure of claim 1 wherein said fluid is a compressible fluid.

4. The procedure of claim 3 wherein said fluid is air.

5. The procedure of claim 1 wherein said fluid is a combination of liquid and gas.

6. The procedure of claim 1 wherein said fluid is, at least in part, an autogenous material.

* * * * *